United States Patent [19]

Drabek et al.

[11] 4,010,227
[45] Mar. 1, 1977

[54] O-ALKYL-S-ALKYL-O-(SUBSTITUTED PHENYL)THIOLPHOSPHATES

[75] Inventors: Jozef Drabek, Allschwil, Switzerland; Manfred Böger, Haltingen, Germany; Odd Kristiansen, Mohlin, Switzerland

[73] Assignee: Ciba-Geigy Corporation, Ardsley, N.Y.

[22] Filed: Aug. 6, 1975

[21] Appl. No.: 601,886

Related U.S. Application Data

[62] Division of Ser. No. 455,458, March 27, 1974, Pat. No. 3,917,752.

[30] Foreign Application Priority Data

Apr. 3, 1973  Switzerland .................. 4737/73
Mar. 5, 1974  Switzerland .................. 3154/74

[52] U.S. Cl. ............................................. 260/940
[51] Int. Cl.² ........................................ C07F 9/18
[58] Field of Search ................................. 260/940

[56] References Cited

UNITED STATES PATENTS 3,839,511   10/1974   Kishino et al. ............ 260/940 X Primary Examiner—Richard L. Raymond
Attorney, Agent, or Firm—Frederick H. Rabin

[57] ABSTRACT

Thiolphosphoric acid esters of the formula

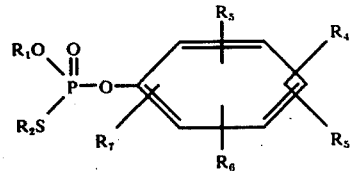

wherein
$R_1$ represents methyl or ethyl,
$R_2$ represents n-propyl, isopropyl, isobutyl or sec.butyl,
$R_3$ represents nitro, cyano, allyl or methylthio,
$R_4$ represents hydrogen, chlorine, bromine, methyl or nitro, and
$R_5$, $R_6$ and $R_7$ each represent chlorine, bromine or methyl, processes for their preparation and their use in pest control.

1 Claim, No Drawings

O-ALKYL-S-ALKYL-O-(SUBSTITUTED PHENYL)THIOLPHOSPHATES

This is a division of application Ser. No. 455,458 filed on Mar. 27, 1974, now U.S. Pat. No. 3,917,752.

The present invention relates to thiolphosphoric acid esters, to processes for their preparation, and to their use in pest control.

The thiolphosphoric acid esters have the formula

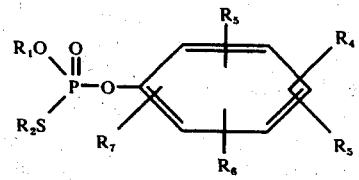

wherein
$R_1$ represents methyl or ethyl,
$R_2$ represents n-propyl, isopropyl, isobutyl or sec.-butyl,
$R_3$ represents nitro, cyano, allyl or methylthio,
$R_4$ represents hydrogen, chlorine, bromine, methyl or nitro, and
$R_5$, $R_6$ and $R_7$ each represent chlorine, bromine, or methyl.

Compounds of formula I preferred on account of their action are those wherein
$R_1$ represents ethyl,
$R_2$ represents n-propyl or sec.-butyl,
$R_3$ represents allyl, nitro, cyano or methylthio,
$R_4$ represents hydrogen, chlorine, bromine or methyl, and
$R_5$, $R_6$ and $R_7$ each represent chlorine, bromine or methyl.

The compounds of formula I can be prepared by the following methods known per se:

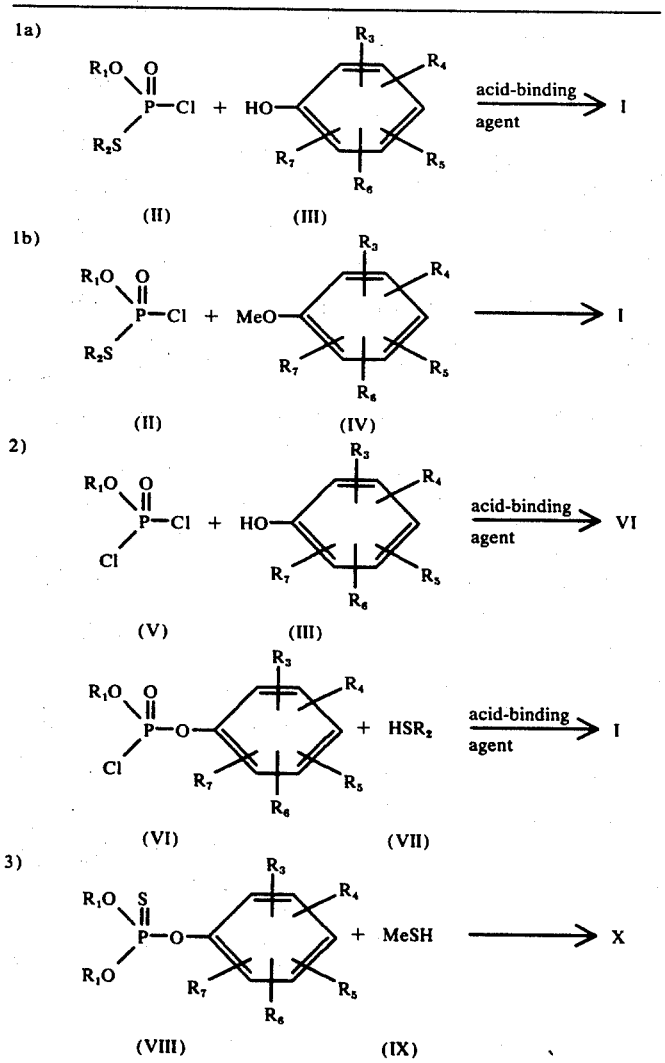

-continued

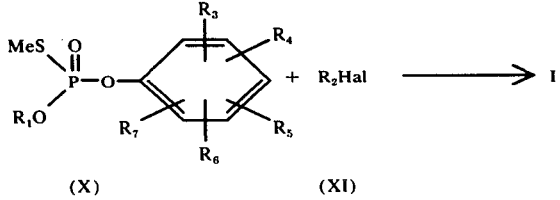

In formulae II to XI, the symbols $R_1$ to $R_7$ have the meanings defined for formula I, and Me stands for an alkali metal, particularly for sodium or potassium, ammonium or alkylammonium, and Hal for a halogen atom, such as fluorine, chlorine, bromine or iodine.

Suitable acid-binding agents are tertiary amines, e.g., trialkylamines, pyridine or dialkylanilines; inorganic bases such as hydrides or hydroxides; and carbonates and bicarbonates of alkali metals and alkaline-earth metals.

It is sometimes necessary to use catalysts in the reactions, such as, e.g., copper or copper chloride. The processes 1a and 1b, 2 and 3 are performed at a reaction temperature of between 0° and 130° C, under normal pressure, and in solvents or diluents.

Applicable solvents or diluents are, e.g., ethers and ethereal compounds, such as diethyl ether, dipropyl ether, dioxane or tetrahydrofuran; amides such as N,N-dialkylated carboxylic acid amides; aliphatic, aromatic as well as halogenated hydrocarbons, especially benzene, toluene, xylenes, chloroform or chlorobenzene; nitriles such as acetonitriles; dimethylsulphoxide, ketones such as acetone or methyl ethyl ketone; and water. Also ethanol is suitable in the case of process 3.

The starting materials of formula II, V and VIII can be prepared by methods analogous to known methods, e.g., analogous to those described in "Organic Reactions II," pp. 1 to 48.

The compounds of formula I have a broad biocidal action, and are therefore suitable for the control of diverse plant and animal pests. Compared with analogous compounds from the German Offenlegungsschriften Nos. 1,768,452 and 2,163,391, the compounds of formula I have a surprisingly better action against, for example, biting insects.

The said compounds are suitable for the control of all development stages, such as, e.g., eggs, larvae, pupae, nymphs and adults of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae, as well as acarids of the families: Ixodidae, Argasidae, Tetranychidae and Dermanyssidae.

The insecticidal or acaricidal action can be appreciably broadened and adapted to suit given circumstances by the addition of other insecticides and/or acaricides. Suitable additives are, for example:
  organic phosphorus compounds,
  nitrophenols and derivatives thereof,
  formamidines,
  carbamates and
  chlorinated hydrocarbons.

The compounds of formula I can be used on their own or together with suitable carriers and/or additives. Suitable carriers and additives may be solid or liquid, and they correspond to the substances common in formulation practice, such as, e.g., natural or regenerated substances, solvents, dispersing agents, wetting agents, adhesives, thickners, binders and/or fertilizers.

For application, the compounds of formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:
solid preparations:
  dusts, scattering agents, granulates, coated granulates, impregnated granulates and homogeneous granulates;
liquid preparations
  a. water-dispersible active-substance concentrates:
    wettable powders, pastes or emulsions;
  b. solutions.

The content of active substance in the described agents is between 0.1 and 95%; it is to be mentioned in this respect, however, that concentrations of up to 99.5% can be used where the said agents are applied from an aeroplane or by means of other suitable application devices.

The active substances of formula I can be formulated, for example, as follows:

DUSTS

The following substances are used in the preparation of a) a 5% dust, and b) a 2% dust:
  a. 5 parts of active substance,
    95 parts of talcum;
  b. 2 parts of active substance,
    1 part of highly dispersed silicic acid,
    97 parts of talcum.
The active substances are mixed and ground with the carriers.

GRANULATE

The following substances are used to prepare a 5% granulate:
  5 parts of active substance,
  0.25 part of epichlorohydrin,
  0.25 part of cetyl polyglycol ether, 3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone subsequently evaporated off in vacuo.

WETTABLE POWDER

The following constituents are used for the preparation of (a) a 40%, (b) and (c) a 25%, and (d) a 10% wettable powder:
a. 40 parts of active substance,
   5 parts of sodium lignin sulphonate,
   1 part of sodium dibutyl-naphthalene sulphonate,
   54 parts of silicic acid;
b. 25 parts of active substance,
   4.5 parts of calcium lignin sulphonate,
   1.9 parts of Champagne chalk/hydroxyethyl cellulose mixture (1:1),
   1.5 parts of sodium dibutyl naphthalene sulphonate,
   19.5 parts of silicic acid,
   19.5 parts of Champagne chalk,
   28.1 parts of kaolin;
c. 25 parts of active substance,
   2.5 parts of isooctylphenoxy-polyoxyethylene-ethanol,
   1.7 parts of Champagne chalk/hydroxyethyl cellulose mixture (1:1),
   8.3 parts of sodium aluminum silicate,
   16.5 parts of kieselguhr,
   46 parts of kaolin;
d. 10 parts of active substance,
   3 parts of a mixture of the sodium salts of saturated fatty alcohol sulphates,
   5 parts of naphthalenesulphonic acid/formaldehyde condensate,
   82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

EMULSIFIABLE CONCENTRATES

The following substances are used to prepare (a) a 10% and (b) a 25% emulsifiable concentrate:
a. 10 parts of active substance,
   3.4 parts of epoxidized vegetable oil,
   3.4 parts of a combination emulsifier consisting of fatty alcohol polyglycol ether and alkylarylsulphonate calcium salt,
   40 parts of dimethylformamide,
   43.2 parts of xylene;
b. 25 parts of active substance,
   2.5 parts of epoxidized vegetable oil,
   10 parts of an alkylarylsulphonate/fatty alcohol polyglycol ether mixture,
   5 parts of dimethylformamide,
   57.5 parts of xylene.

From these concentrates it is possible to prepare, by dilution with water, emulsions of any desired concentration.

SPRAY

The following constituents are used to prepare a 5% spray:

5 parts of active substance,
1 part of epichlorhydrin,
94 parts of ligroin (boiling limits 160° – 190° C).

EXAMPLE 1

Preparation of O-ethyl-S-n-propyl-O-(2-allyl-3,4,6-trichlorophenyl)-thiolphosphate 20.3 g of O-ethyl-S-propyl-thiolphosphoric acid chloride is added dropwise at 10° – 15° C, with continuous stirring, to a solution of 23.7 g of 2-allyl-3,4,6-trichlorophenol in 150 ml of benzene and 10.12 g of triethylamine. The mixture is stirred for a further 12 hours at room temperature; it is then washed with water, with 3% Na$_2$CO$_3$-solution and again with water, and subsequently dried over anhydrous sodium sulphate. The benzene is distilled off, and the residue dried for 30 minutes at 80° C under 0.1 Torr to obtain the compound of the formula

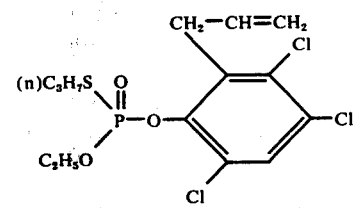

in the form of oil having a refractive index of $n_D^{20} = 1.5529$.

The following further compounds are prepared in an analogous manner:

| Compounds | Physical data |
|---|---|
| (structure with OC$_2$H$_5$, SC$_3$H$_7$(i), CH$_2$—CH=CH$_2$, Cl, Cl, Cl) | $n_D^{20} = 1.5500$ |
| (structure with OC$_2$H$_5$, SC$_4$H$_9$(i), CH$_2$—CH=CH$_2$, Cl, Cl, Cl) | $n_D^{20} = 1.5452$ |
| (structure with OC$_2$H$_5$, SC$_3$H$_7$(n), CH$_2$—CH=CH$_2$, Cl, Cl, Cl) | $n_D^{20} = 1.5514$ |

| Compounds | Physical data |
|---|---|
| 2,3-dichloro-4-chloro-6-(allyl)phenyl O-ethyl S-sec-butyl phosphorothiolate (3,4-Cl₂, 2,3-Cl₂ ring with CH₂-CH=CH₂, OC₂H₅, SC₄H₉(sek.)) | $n_D^{20} = 1{,}5443$ |
| 4-chloro-3-methyl-5-methyl-2-allylphenyl O-ethyl S-n-propyl phosphorothiolate | $n_D^{20} = 1{,}5347$ |
| 2,6-dichloro-4-bromo-3-allyl phenyl O-ethyl S-n-propyl phosphorothiolate | $n_D^{20} = 1{,}5644$ |
| 4-cyano-3,5-dimethyl-2-chlorophenyl O-ethyl S-n-propyl phosphorothiolate | $n_D^{20} = 1{,}5410$ |
| 4-chloro-3-methyl-5-methyl-2-nitrophenyl O-ethyl S-n-propyl phosphorothiolate | M.P.: 50° C |
| 3,4-dimethyl-2-nitrophenyl O-ethyl S-n-propyl phosphorothiolate | $n_D^{20} = 1{,}5296$ |
| 2-bromo-3,5-dimethyl-4-methylthiophenyl O-ethyl S-n-propyl phosphorothiolate | $n_D^{20} = 1{,}5686$ |
| 2-bromo-3,5-dimethyl-4-methylthiophenyl O-ethyl S-sec-butyl phosphorothiolate | $n_D^{20} = 1{,}5592$ |
| 2,6-dibromo-3,5-dimethyl-4-methylthiophenyl O-ethyl S-n-propyl phosphorothiolate | $n_D^{20} = 1{,}5900$ |
| 2,6-dinitro-3,4,5-trimethylphenyl O-ethyl S-n-propyl phosphorothiolate | $n_D^{20} = 1{,}5283$ |
| 2,4-dibromo-6-bromo-3-cyanophenyl O-ethyl S-n-propyl phosphorothiolate | $n_D^{20} = 1{,}5880$ |
| 2,3,5-trichloro-4-cyanophenyl O-ethyl S-n-propyl phosphorothiolate | $n_D^{22} = 1{,}5546$ |

EXAMPLE 2

A. Insecticidal stomach poison action

Cotton and potato plants were sprayed with a 0.05% aqueous active-substance emulsion (obtained from a 10% emulsifiable concentrate).

After the drying of the obtained coating, *Spodoptera littoralis* or *Heliothis virescens* larvae $L_3$ were placed on the cotton plants, and *Colorada beetle* larvae (*Leptinotarsa decemlineata*) on the potato plants. The test was carried out at 24° C with 60% relative humidity.

The compounds according to Example 1 exhibited in the above test a good insecticidal stomach poison action against *Spodoptera littoralis*, *Heliothis* and *Leptinotarsa decemlineata* larvae.

EXAMPLE 3

Action against ticks

A. *Rhipicephalus bursa*

In each case, 5 adult ticks or 50 tick larvae were placed into a small glass test tube, and the test tubes then immersed for 1 to 2 minutes in 2 ml of an aqueous emulsion from a dilution series of 100, 10, 1 and 0.1 ppm of test substance. The tubes were then sealed with a standardized cotton plug, and inverted so that the active-substance emulsion could be absorbed by the cotton wool.

An evaluation in the case of the adults was made after 2 weeks, and in the case of the larvae after 2 days. There were two repeats for each test.

B. *Boophilus microplus* (larvae)

With a dilution series analogous to that in Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 4

Acaricidal action

*Phaseolus vulgaris* (plants) were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflowing of the spray liquor. An assessment was made after 2 to 7 days, by examination under a binocular, of living larvae and dead larvae, adults and eggs, and the results expressed in percentages. The treated plants were kept during the "holding time" in greenhouse compartments at 25° C.

The compounds according to Example 1 were effective in the above test against adults, larvae and eggs of *Tetranychus urticae*.

What we claim is:
1. O-Ethyl-S-n-propyl-O-(2-chloro-4-cyano-3,5-dimethylphenyl)-thiolphosphate.

* * * * *